United States Patent [19]

Wurtman et al.

[11] Patent Number: 4,626,527

[45] Date of Patent: Dec. 2, 1986

[54] PROCESS FOR UTILIZING CHOLINE TO SUSTAIN MUSCULAR PERFORMANCE

[75] Inventors: Richard J. Wurtman, Boston; Lydia Conlay, Nahant; Krzysztof Blusztajn, Cambridge, all of Mass.

[73] Assignee: Massachusetts Institute of Technology, Cambridge, Mass.

[21] Appl. No.: 780,053

[22] Filed: Sep. 28, 1985

[51] Int. Cl.$^4$ ............................................ A61K 31/685
[52] U.S. Cl. ........................................................ 514/78
[58] Field of Search ............................................ 514/78

[56] References Cited

U.S. PATENT DOCUMENTS 4,456,598  6/1984  Growdon et al. ..................... 514/78

Primary Examiner—Stanley J. Friedman
Attorney, Agent, or Firm—Paul J. Cook

[57] ABSTRACT

Choline or a natural or synthetic compound that dissociates to form choline is administered to a patient who has or is about to participate in major exercise in order to decrease fatigue by increasing acetylcholine levels in the brain or other tissues. The term "fatigue" as used herein means the subjective feeling of tiredness as well as the fatigue of muscles and the actual decrease of performance.

4 Claims, No Drawings

PROCESS FOR UTILIZING CHOLINE TO SUSTAIN MUSCULAR PERFORMANCE

BACKGROUND OF THE INVENTION

This invention relates to a process for the administration of choline, or natural or synthetic compounds that dissociate to form choline in order to reduce fatigue in a patient who has or is about to participate in major exercise by increasing acetylcholine levels in brain and other tissues.

There are a number of diseases which affect acetylcholine-containing neurons in the brain or other tissues, and which are treated by drugs that cause undesired side effects by diminishing acetylcholine's release; there also exist diseases now treated by other durgs in which the potency and/or efficacy of the drugs could be improved by combining them with choline or natural or synthetic compounds that dissociate to form choline in order thereby to enhance the release of acetylcholine. Such diseases include both those primarily involving the brain (e.g., diseases of higher cortical functions; psychiatric illnesses; movement disorders) and those involving the peripheral nervous system (e.g., neuromuscular disorders).

We have shown that choline administered by injection or by dietary supplementation increases blood choline levels in the rat; this, in turn, increases choline levels in cholinergic neurons within the brain and elsewhere in the body, thereby accelerating the synthesis of acetylcholine, increasing tissue acetylcholine levels, and increasing the amounts of acetylcholine released into brain synapses. In human beings, oral doses of choline or of lecithin, a naturally-occurring compound that dissociates the choline were found to cause dose-related increases in blood choline levels of sufficient magnitude (based on the studies on rats) to enhance brain acetylcholine synthesis and release; choline levels in the cerebrospinal fluid also rose in parallel. Prior to our invention, it had not been known that major exercise has an effect on the blood levels of choline in a patient.

SUMMARY OF THE INVENTION

This invention is based upon the discovery that major exercise produces a significant reduction of choline blood levels in a patient. Accordingly, choline or a physiologicallyacceptable natural or synthetic compound that dissociates to form choline is administered to a parient about to participate in major exercise to provide a prophylactic effect against fatigue or is administered after major exercise to reduce fatigue. The choline may be administered orally such as in tablet, capsule or liquid form or parenterally by intravenous, intramuscular or subcutaneous injection.

DETAILED DESCRIPTION OF SPECIFIC EMBODIMENTS

In accordance with this invention, choline or a compound that dissociates to form choline is orally administered to a patient prior to or subsequent to major exercise in order to increase blood levels of choline, and thereby to increase the level of acetylcholine in the brain and in muscle tissue. The acetylcholine is synthesized from choline and acetyl CoA in a reaction catalyzed by choline acetyltransferase (CAT).

The discovery that blood choline levels fall markedly after major exercise is surprising. One would expect choline levels, like plasma amino acid levels, to rise since choline and the amino acids are destroyed by the liver and exercise decreases the amount of blood sent to the liver.

The choline can be administered as choline salts, such as the chloride bitratrate or the like, or as a compound that dissociates to choline, such as acylglycerophosphocholine, e.g., lecithin, lysolecithin, glycerophosphocholine, mixtures thereof or the like. By the term "acylglycerophosphocholine" as used herein is meant a compound of the formula:

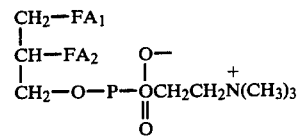

wherein $FA_1$ and $FA_2$ can be the same or different and are fatty acid residues having from 6–26 carbon atoms, usually 16–24 carbon atoms and can be saturated or unsaturated such as palmitic acid, palmitoleic acid, stearic acid, oleic acid, linoleic acid, eicosanoic acid, arachidonic acid, docosahexaenoic acid, eicosapentaenoic acid, linolenic acid, mixtures thereof or the like. The fatty acid residues of the acyglycerophosphocholine can be varied by treatment with the acyglycerophosphocholine, e.g., a lecithin with phospholipase A1 or A2 (to cleave one fatty acid residue) or then phospholipase B (when desired to cleave both fatty acid residues) and then contacting the cleaved compound with the fatty acid of choice. These choline producing compounds also can be administered to patients having lower than normal plasma choline levels, such as patinets experiencing renal dialysis. It is preferred to employ an acyglycerophosphocholine, e.g., lecithin as the choline source since it is not degraded in the gut in contrast to choline. The choline or compound that dissociates to choline is administered so that a choline level of at least about 20–30 nanomoles/ml and usually between about 10 and 50 nmoles/ml is attained in the patient's bloodstream. For example, when administering choline chloride in the form of capsules or tablets, suitable dosages are from about 1 to 30 g/day, preferably 3–20 g/day taken in divided doses 500 to 1000 mg/cap or tab. When choline chloride is administered in liquid form admixed with a conventional liquid carrier such as a sweetened elixir or the like, from about 1 to 10 grams/15 ml, preferably from about 2 to 5 grams/15 ml can be utilized. When utilizing lecithin in a liquid carrier, it is administered in amounts of between about 0.1 and 50 grams/day. When lecithin is administered in granular form, as a tablet or in a capsule, it is employed in amounts of between 0.1 and 100 g/day, usually between about 30 and 50 g/day. Normally, lecithin is not available as a pure compound and is available in admixture with other phospholipids wherein the lecithin comprises about 20–30 weight percent of the mixture.

The following example illustrates the present invention and is not intended to limit the same.

EXAMPLE I

Men and women, planning to run the Boston Marathon, were used in this study. No restrictions were made concerning age, sex, medical history/drug therapy or food consumption. Just prior to the start of the race, the 23 subjects completed a questionnaire and a blood sample was taken. Blood wad immediately spun to separate the plasma, and the plasma was frozen and stored at −70°. 21 of the 23 subjects finished the race. They were immediately examined, and blood was again removed for choline assay (and treated as above). Again, they completed a questionnaire concerning food consumption during the race, finish time, gastrointestinal symptons, etc. The blood was assayed for choline radioenzymatically.

As shown in Table I, choline declined in all subjects completing the Marathon. The decline was approximately 35% on average, and the probability that the change was due to chance alone was less than 0.001%. Data from individual subjects are shown in the figures below.

TABLE I

Plasma Choline Levels (nM/ml) of 23 Marathon Runners

| Subject | Before | After |
|---|---|---|
| 1 | 16.18 | 6.30 |
| 2 | 9.70 | 5.27 |
| 3 | 7.55 | |
| 4 | 11.77 | 5.48 |
| 5 | 8.35 | 6.33 |
| 6 | 7.69 | 6.15 |
| 7 | 7.79 | 6.26 |
| 8 | 9.85 | 6.59 |
| 9 | 9.41 | 6.40 |
| 10 | 12.85 | |
| 11 | | 8.57 |
| 12 | 10.54 | 5.76 |
| 13 | 12.16 | 7.03 |
| 14 | | |
| 15 | | |
| 16 | 11.41 | 8.12 |
| 17 | 9.57 | 2.98 |
| 18 | 10.58 | 5.61 |
| 19 | 9.50 | 5.74 |
| 20 | 7.55 | 6.75 |
| 21 | 9.73 | 5.85 |
| 22 | 9.51 | |
| 23 | 11.14 | 7.04 |
| 24 | 10.14 | 6.24 |
| 25 | 2.05 | 1.15 |

We claim:

1. The process of reducing fatigue caused by major exercise in a patient about to participate in major exercise or in a patient having completed major exercise which comprises administering to said patient an amount of a compound effective to raise the bloodstream choline level of the patient to between about 10 and 50 nanomoles/ml and to release adequate amounts of brain acetylcholine selected from the group consisting of choline, a salt of choline, lysolecithin, an acyglycerophosphocholine, having the formula:

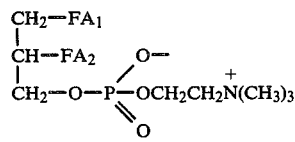

wherein $FA_1$ and $FA_2$ can be the same or different and are fatty acid residues having from 6–26 carbon atoms, glycerophosphocholine and mixtures thereof.

2. The process of claim 1 wherein the compound is an acyglycerophosphocholine.

3. The process of claim 1 wherein the acyglycerophosphocholine is lecithin.

4. The process of claim 1 wherein the compound is choline chloride.

* * * * *